(12) United States Patent
Kunitomi et al.

(10) Patent No.: US 11,142,731 B2
(45) Date of Patent: Oct. 12, 2021

(54) PLATE

(71) Applicant: TOPPAN PRINTING CO., LTD., Taito-ku (JP)

(72) Inventors: Tomoko Kunitomi, Taito-ku (JP); Yoichi Makino, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 683 days.

(21) Appl. No.: 15/854,355

(22) Filed: Dec. 26, 2017

(65) Prior Publication Data

US 2018/0119078 A1    May 3, 2018

Related U.S. Application Data

(63) Continuation of application No. PCT/JP2016/068803, filed on Jun. 24, 2016.

(30) Foreign Application Priority Data

Jun. 26, 2015 (JP) .............................. JP2015-129012

(51) Int. Cl.
*B01L 3/00* (2006.01)
*C12M 1/34* (2006.01)
(Continued)

(52) U.S. Cl.
CPC ........... *C12M 1/34* (2013.01); *B01L 3/50851* (2013.01); *C12M 1/00* (2013.01); *C12Q 1/6825* (2013.01);
(Continued)

(58) Field of Classification Search
CPC ............. B01L 2200/0689; B01L 3/502; B01L 2300/0832
(Continued)

(56) References Cited

U.S. PATENT DOCUMENTS

| | | | |
|---|---|---|---|
| 8,222,047 B2 | 7/2012 | Duffy et al. | |
| 2009/0179146 A1* | 7/2009 | Lomas | B01L 3/563 |
| | | | 250/282 |
| 2012/0196774 A1 | 8/2012 | Fournier et al. | |

FOREIGN PATENT DOCUMENTS

| | | |
|---|---|---|
| JP | 2007-121130 A | 5/2007 |
| JP | 2009-047438 A | 3/2009 |
| JP | 4911592 B2 | 4/2012 |

OTHER PUBLICATIONS

International Search Report dated Aug. 2, 2016 in PCT/JP2016/068803, filed Jun. 24, 2016.

* cited by examiner

*Primary Examiner* — Natalia Levkovich
(74) *Attorney, Agent, or Firm* — Oblon, McClelland, Maier & Neustadt, L.L.P.

(57) ABSTRACT

An analytical device includes a plate including a first substrate having a front surface and a back surface and a second substrate facing the back surface of the first substrate such that at least one detection space observable from outside is formed between the second substrate and the back surface of the first substrate, and an adapter. The first substrate has a first port having a through hole formed through the front surface and communicated with the detection space for delivering a liquid-containing substance into the detection space, the first substrate has a second port having a through hole formed through the front surface and communicated with the detection space for discharging a liquid-containing substance or a gas from the detection space, and the adapter is attachable to and detachable from the first port and the second port, and the front surface of the first substrate without the adapter is flat.

20 Claims, 16 Drawing Sheets

(51) Int. Cl.
*C12M 1/00* (2006.01)
*G01N 21/64* (2006.01)
*C12Q 1/6825* (2018.01)
*B01L 7/00* (2006.01)

(52) U.S. Cl.
CPC ......... *G01N 21/64* (2013.01); *G01N 21/6452* (2013.01); *B01L 3/563* (2013.01); *B01L 7/52* (2013.01); *B01L 2200/026* (2013.01); *B01L 2300/069* (2013.01); *B01L 2300/0654* (2013.01); *B01L 2300/0819* (2013.01)

(58) Field of Classification Search
USPC .................................................. 422/551, 554
See application file for complete search history.

PLATE

CROSS-REFERENCE TO RELATED APPLICATIONS

The present application is a continuation of International Application No. PCT/JP2016/068803, filed Jun. 24, 2016, which is based upon and claims the benefits of priority to Japanese Application No. 2015-129012, filed Jun. 26, 2015. The entire contents of these applications are incorporated herein by reference.

BACKGROUND OF THE INVENTION

Field of the Invention

The present invention is directed to a general-purpose plate including an adaptor for detecting an in vivo substance, and relates to a technique preferably used for a nucleic acid extraction kit.

Discussion of the Background

Detection of in vivo substances, such as nucleic acids and proteins, has been conducted to determine the disease condition or a change in the disease condition, the degree of recovery, and the physical predisposition. According to systems that have been developed in recent years, in vivo substances in a sample are detected on a molecular unit basis or a cellular unit basis. For example, Patent Literatures (PTLs) 1 and 2 use a member with a number of micropores to detect molecules or cells by introducing them into the micropores.

As disclosed in PTL 3, it is known that oil is used for covering a sample in such a system.

Other than these systems, commercially available systems are also known.

Such a system, however, requires a large amount of oil for covering a sample, as disclosed in PTL 3. Furthermore, being incorporated with a waste reservoir, such a system uses a base which needs a lateral or longitudinal space, besides a detection or reaction area. Accordingly, a dedicated device is necessary for detecting in vivo substances, and thus such a system is likely to have low versatility.

As disclosed in PTL 1, a system has been developed for research use, which is configured to use polydimethylsiloxane (PDMS). However, the base material of this system needs a lateral flow path, or the inlet for samples and the area for the waste liquid of this system have holes only, and thus such a system is likely to have low practicality.

As described above, commercial products are likely to have low versatility although they may have high practicality. On the other hand, products for research use are likely to have low practicality although they may have higher versatility than commercial products.

PTL 1: JP 4911592 B
PTL 2: U.S. Pat. No. 8,222,047 B
PTL 3: US 2012/0196774 A

SUMMARY OF THE INVENTION

According to an aspect of the present invention, an analytical device includes a plate including a first substrate having a front surface and a back surface and a second substrate facing the back surface of the first substrate such that at least one detection space observable from outside is formed between the second substrate and the back surface of the first substrate, and an adapter. The first substrate has a first port having a through hole formed through the front surface and communicated with the detection space for delivering a liquid-containing substance into the detection space. The first substrate has a second port having a through hole formed through the front surface and communicated with the detection space for discharging a liquid-containing substance or a gas from the detection space. The adapter is attachable to and detachable from the first port and the second port, and the front surface of the first substrate without the adapter is flat.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1:
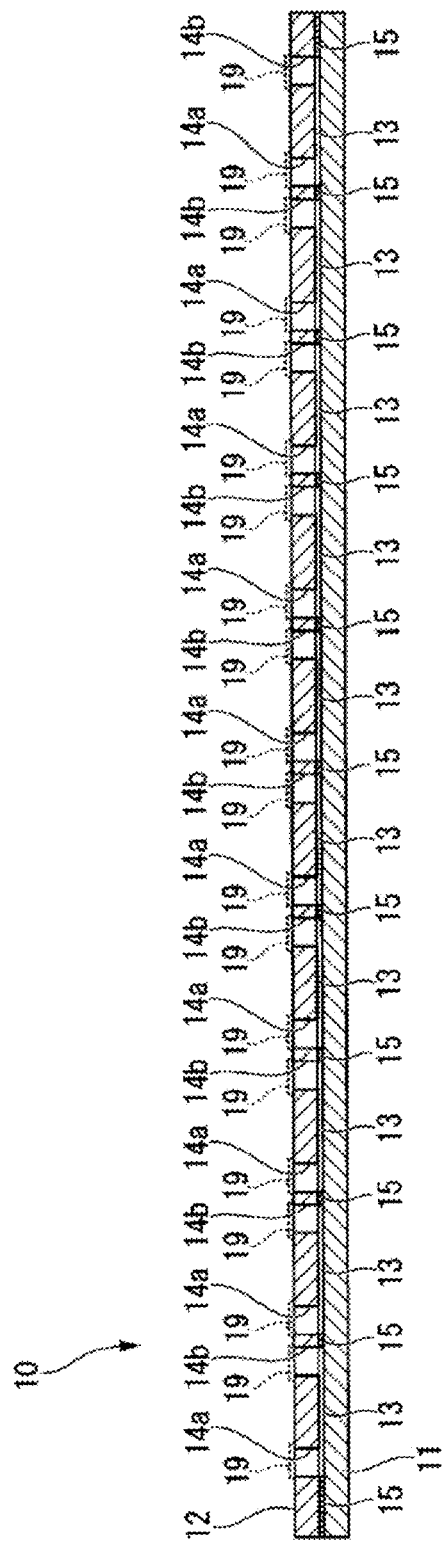
FIG. 1 is a cross-sectional view of a plate, according to an embodiment of the present invention.

The embodiments will now be described with reference to the accompanying drawings, wherein like reference numerals designate corresponding or identical elements throughout the various drawings.

A plate according to an embodiment of the present invention will be described below with reference to the drawings.

Figure 2:
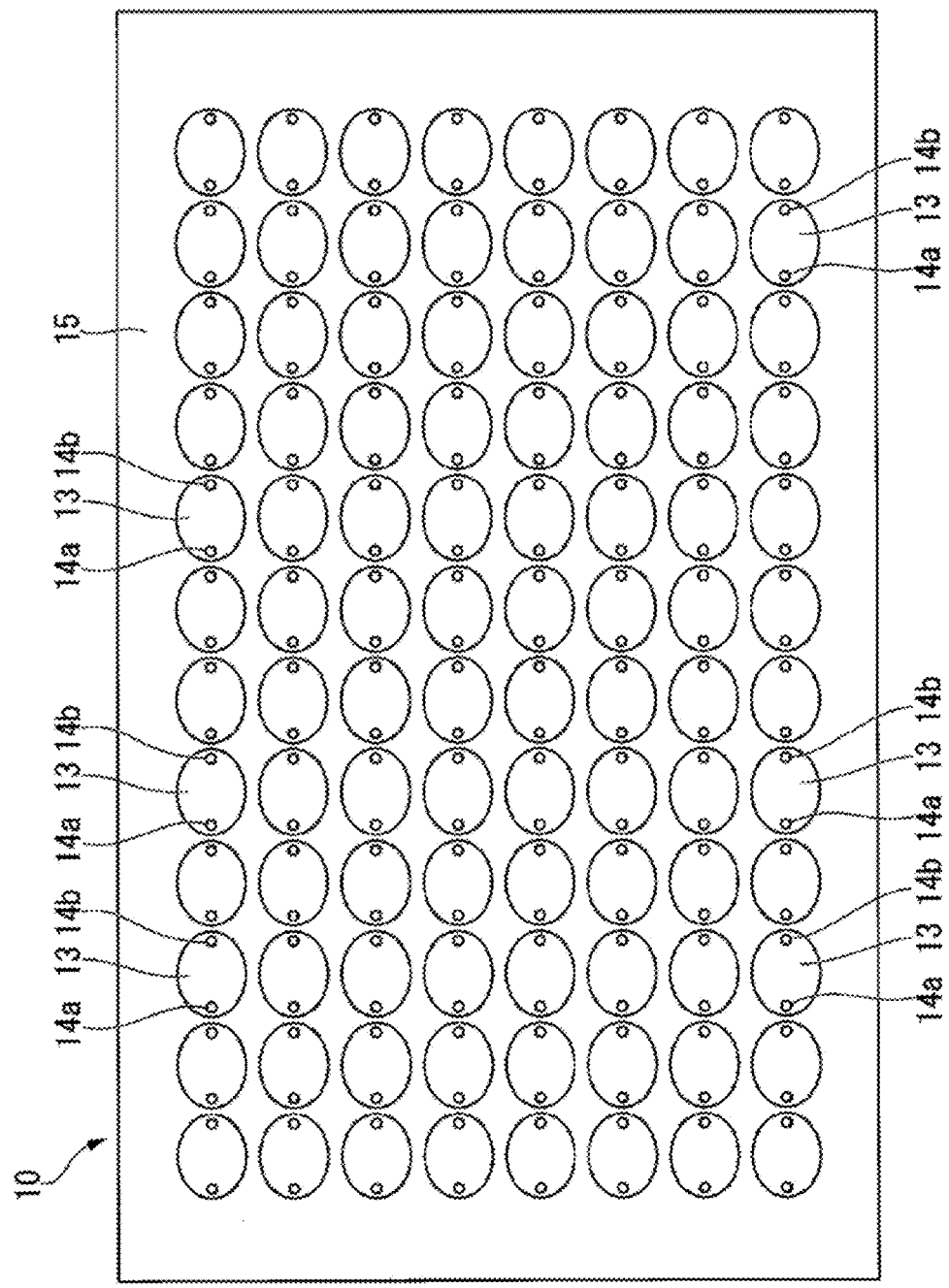
FIG. 2 is a schematic plan view of a plate, according to an embodiment of the present invention.
Figure 3:
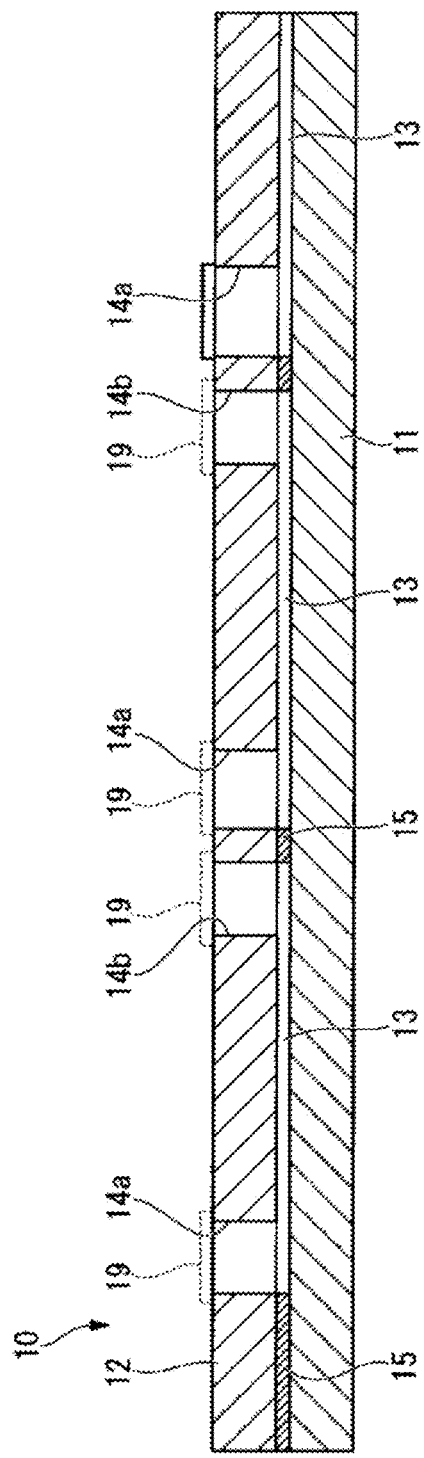
FIG. 3 is an enlarged cross-sectional view of FIG. 1.

FIG. 1 is a cross-sectional view illustrating a plate of the present embodiment. FIG. 2 is a schematic plan view illustrating the plate of the present embodiment. FIG. 3 is an enlarged cross-sectional view of FIG. 1, that is, a cross-sectional view illustrating the plate of the present embodiment. In FIGS. 1 to 3, a reference sign 10 denotes a plate.

As illustrated in FIGS. 1 and 3, the plate 10 according to the present embodiment includes: two substrates 11 and 12 facing each other and bonded together by an adhesive layer 15, while being distanced from each other by the adhesive layer 15; and a detection space 13 formed between the substrates 11 and 12.

At least one of the substrates 11 and 12 has transparency to enable observation and measurement from outside. At least one of the substrates 11 and 12 is a plate-like member made of a substantially transparent material. Examples of the material of the substrates 11 and 12 include glass and plastic.

As illustrated in FIG. 2, in the plate 10 of the present embodiment, a number of detection spaces 13 are arranged in a matrix form in plan view. None of these detection spaces 13 is in communication with an adjacent detection space 13, and thus the individual detection space 13 is independent.

The detection space 13 may have a surface having one or more, preferably 100 or more pores each having a capacity of 1 pl or less. These pores each having a capacity of 1 pl or less may be provided to the front surface of the substrate 12, or may be provided to the front surface of the substrate 11. Note that these pores each having a capacity of 1 pl or less may be provided to a separate member (for example, a film) and this separate member may be provided in the detection space 13 by, for example, being attached to the front surface of the substrate 11 or 12.

The substrate (the first substrate) 12, serving as a front, has ports (first ports) 14a and ports (second ports) 14b as through holes communicating with the respective detection spaces 13. Hereinafter, each port 14a is described as a through hole for delivering a liquid-containing substance into the detection space 13. Also, each port 14b is described as a through hole for discharging a gas or a liquid-containing substance from the detection space 13.

Which of the ports 14a and 14b is used for delivery or discharge can be determined as desired.

The substrate 12 needs to have at least two through holes, such as the ports 14a and 14b, communicating with the detection space 13 and serving respectively as an inlet and an outlet for a sample. The through holes serving as the ports 14a and 14b may have an inner diameter of approximately 2 mm, and desirably may have a diameter of 2 mm or more.

As illustrated in FIGS. 1 to 3, the ports 14a and 14b are provided at both ends of the detection space 13 serving as a flow path, the ends being preferably located near the respective adjacent detection spaces 13. As illustrated in FIGS. 1 and 3, the ports 14a and 14b are formed orthogonally to the front surface of the substrate 12 so as to extend in the thickness direction of the substrate 12.

As illustrated in FIGS. 1 and 3, these ports 14a and 14b, which are through holes, are each covered with and closed by a film 19 that is detachable or can be cut through. Note that the films 19 are omitted from FIG. 2. The film 19 that is peelable or can be cut through may be bonded to the upper edge portion of each of the ports 14a and 14b throughout the circumference thereof. This film 19 can be bonded by means of an adhesive or by thermocompression. Furthermore, as will be described later, a detachable lid 19A may be used to close each of the ports 14a and 14b.

The adhesive layer 15 is formed to adhere the substrate (the second substrate) 11 with the substrate 12 and to form a side wall that separates the detection spaces 13 from each other. Specifically, the adhesive layer 15 is in the form of a sheet having a number of through holes in plan view. The adhesive layer 15 has a uniform in-plane thickness so as to define the height of the detection space 13.

The substrates 11 and 12 are bonded together using a double-sided tape having a uniform thickness to maintain a space with a uniform thickness. This is how the plate 10 is prepared, including the detection spaces 13 with a uniform in-plane thickness. Alternatively, the substrates 11 and 12 may be bonded together by an adhesive using a spacer so that a uniform thickness is maintained. Other than these methods, thermocompression bonding may be used in the case where the substrates 11 and 12 are made of a resin.

Figure 4:
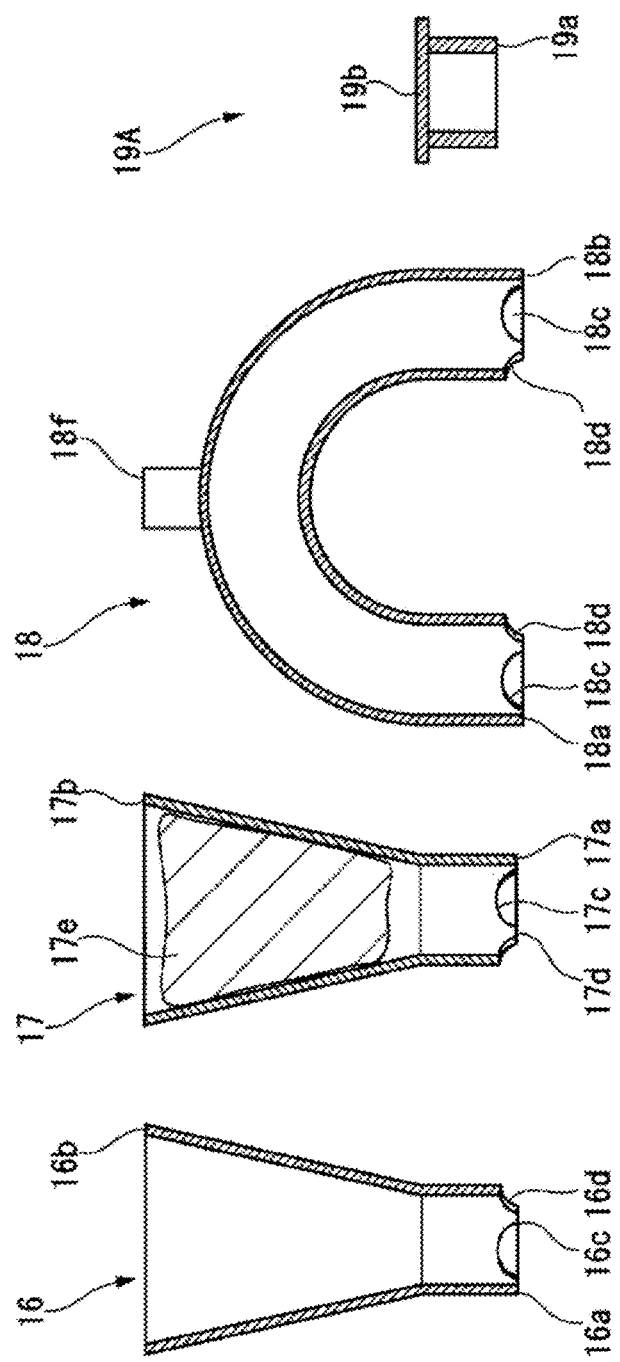
FIG. 4 is a front cross-sectional view of adapters of a plate, according to an embodiment of the present invention.

As illustrated in FIG. 4, the plate 10 of the present embodiment includes adapters 16, 17, and 18 that can be attached to and detached from the ports 14a and 14b.

FIG. 4 is a front cross-sectional view illustrating the adapters of the present embodiment.

These adapters 16, 17, and 18 are attached when a liquid is delivered to and discharged from the detection spaces 13, and are detached when the interior of each detection space 13 is observed with a microscope or the like from outside. Thus, almost all protrusions can be removed from the front surface of the substrate 12.

The adapters 16 and 17 are prepared through resin molding, for example. The adapters 16 and 17 have parts that join their respective ends 16a and 17a to the substrate 12 side through holes, and are configured not to leak liquid when fitted to the through holes. The color of the adapters 16 and 17, and the size thereof other than the joining parts are not limited.

The adapter 16 is configured to deliver a liquid-containing substance into the detection space 13 and can fit to the port 14a.

The adapter 17 is configured to discharge gas or a liquid-containing substance from the detection space 13 and can fit to the port 14b.

The outer shapes of the adapters 16 and 17 are substantially the same. As illustrated in FIG. 4, the adapters 16 and 17 are tubes for establishing communication between the detection space 13 and the outside. The adapters 16 and 17 have the ends 16a and 17a that can fit to the ports 14a and 14b serving as through holes, and have other ends 16b and 17b. The ends 16a and 17a each have a cylindrical shape, and the ends 16b and 17b are open ends having larger diameters than the respective ends 16a and 17a.

The end 16b of the adapter 16 preferably has a shape into which a pipette tip or a dropper tip can be inserted.

The adapter 17 is provided, on the end 17b side, with an effluent reservoir or an effluent absorption sponge 17e as an absorbing means, and is thus configured to absorb the effluent discharged from the detection space 13.

As illustrated in FIG. 4, the adapters 16 and 17 are provided, at their respective ends 16a and 17a, with abutment portions 16c and 17c abutting against the front surface of the substrate 11, and cutout portions 16d and 17d serving as flow paths, when fitted to the respective ports 14a and 14b. These abutment portions 16c and 17c and the cutout portions 16d and 17d form a flow path securing portion.

Smooth movement of liquid or gas toward the cutout portions 16d and 17d and the detection space 13 may be inhibited when the ends 16a and 17a are in intimate contact with the front surface of the substrate 12. The abutment portions 16c and 17c can be provided at the ends 16a and 17a to ensure smooth movement of liquid or gas to the detection space 13 from the adapters 16 and 17. As illustrated in FIG. 4, for example, the abutment portions 16c and 17c can be formed by carving part of the ends 16a and 17a of the respective adapters 16 and 17.

The position, number, and shape of the abutment portions 16c and 17c can be determined as desired. Furthermore, the abutment portions 16c and 17c can be provided integrally with the cutout portions 16d and 17d. The abutment portions 16c and 17c may be omitted.

The cutout portions 16d and 17d may have any shape as long as liquid or the like can be delivered to the detection space 13 without trouble, when injected and discharged by way of the ends 16b and 17b of the adapters 16 and 17. The shape of the cutout portions 16d and 17d can be determined so as to have a cross-sectional area equal to that of the ends 16a and 17a, or to have a cross-section equal to that of the flow path of the detection space 13. Note that the size of the cutout portions 16d and 17d is not limited to the above, as long as the liquid can be delivered, and thus the cutout portions 16d and 17d may have a larger flow-path cross-section or a smaller flow-path cross-section.

It is preferred that a plurality of abutment portions 16c and 17c be provided so that the adapters 16 and 17 are oriented orthogonally to the front surface of the substrate 11 when mounted to the ports 14a and 14b.

The adapter 18 forms a flow path joining and connecting a plurality of detection spaces 13. As illustrated in FIG. 4, the adapter 18 is cylindrically shaped, with both ends 18a and 18b having parallel axial lines and being open in the same direction so as to be fitted to at least one of the port 14a and the port 14b.

As with the ends 16a and 17a of the adapters 16 and 17, the ends 18a and 18b of the adapter 18 are in a cylindrical shape that can fit to the port 14a or 14b serving as a through hole. As illustrated in FIG. 4, the end (the first end) 18a and the end (the second end) 18b are each provided with an abutment portion 18c abutting against the front surface of the substrate 11, and a cutout portion 18d serving as a flow path, when fitted to the port 14a or 14b.

The abutment portion 18c of the adapter 18 can be provided in the same manner as the abutment portions 16c and 17c of the adapters 16 and 17 described above. The abutment portion 18c may be omitted.

As illustrated in FIG. 4, the adapter 18 establishes communication between adjacent detection spaces 13 or distant detection spaces 13, depending on the positions of the detection spaces 13 to be in communication. Thus, the distance between both ends 18a and 18b is determined according to the positions of the detection spaces 13 to be in communication.

As illustrated in FIG. 4, the adapter 18 includes a grip portion 18f at a middle position on a side opposite of the open side of both ends 18a and 18b. The grip portion 18f can improve the handleability of the adapter 18.

The adapter 18 may be formed through resin molding, or may be formed of an elastic material such as a silicone tube. As with the adapters 16 and 17, joining parts between the adapter 18 and the through holes serving as the ports 14a and 14b need to be configured not to leak liquid. The color of the adapter 18, and the size thereof other than the joining parts are not limited. When the adapter 18 is transparent, the presence or absence or the flowing state of a liquid-containing substance can be visually recognized.

As illustrated in FIG. 4, the lid 19A fits to the port 14a or 14b to seal the detection space 13. The lid 19A has an end 19a in a cylindrical shape that can fit to the port 14a or 14b serving as a through hole, and the other end closed by a lid portion 19b. The height of the cylindrical portion of the end 19a is preferably designed to be smaller than the thickness of the substrate 12 so that the cylindrical portion does not protrude into the detection space 13.

A method of using the plate 10 of the present embodiment will be described below.

Figure 5:
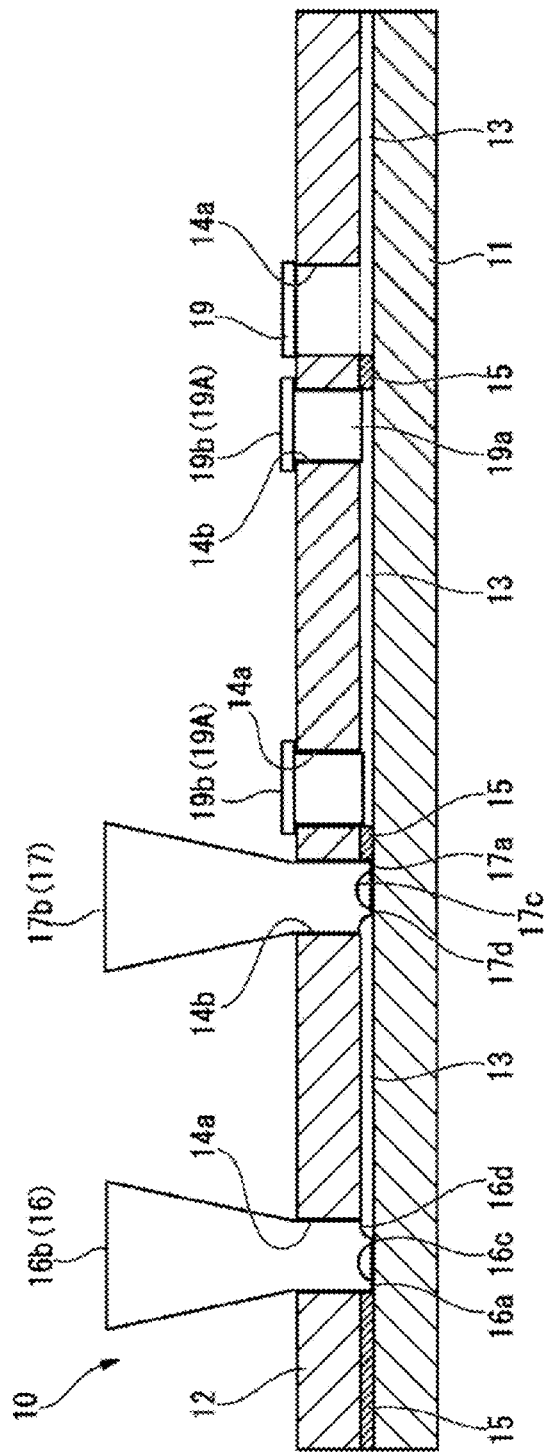
FIG. 5 is a cross-sectional view illustrating an example of a state where adapters are attached to a plate, according to an embodiment of the present invention.

FIG. 5 is a cross-sectional view illustrating an example of a state where the adapters are attached to the plate 10 of the present embodiment.

The following description is focused on the case of using only a single detection space 13 of the plate 10 of the present embodiment. In this case, as illustrated in FIG. 5, the adapter 16 is mounted to the port 14a and the adapter 17 is mounted to the port 14b, with respect to the single detection space 13 to be used. Lids 19A can be mounted to the respective ports 14a and 14b in communication with the detection space 13 not to be used and located adjacent to the detection space 13 to be used, so that the ports 14a and 14b are hermetically closed. Although not illustrated, the ports 14a and 14b are hermetically closed by the films 19 that can be cut through by the adapters 16 and 17 to mount them to the ports.

Figure 6:
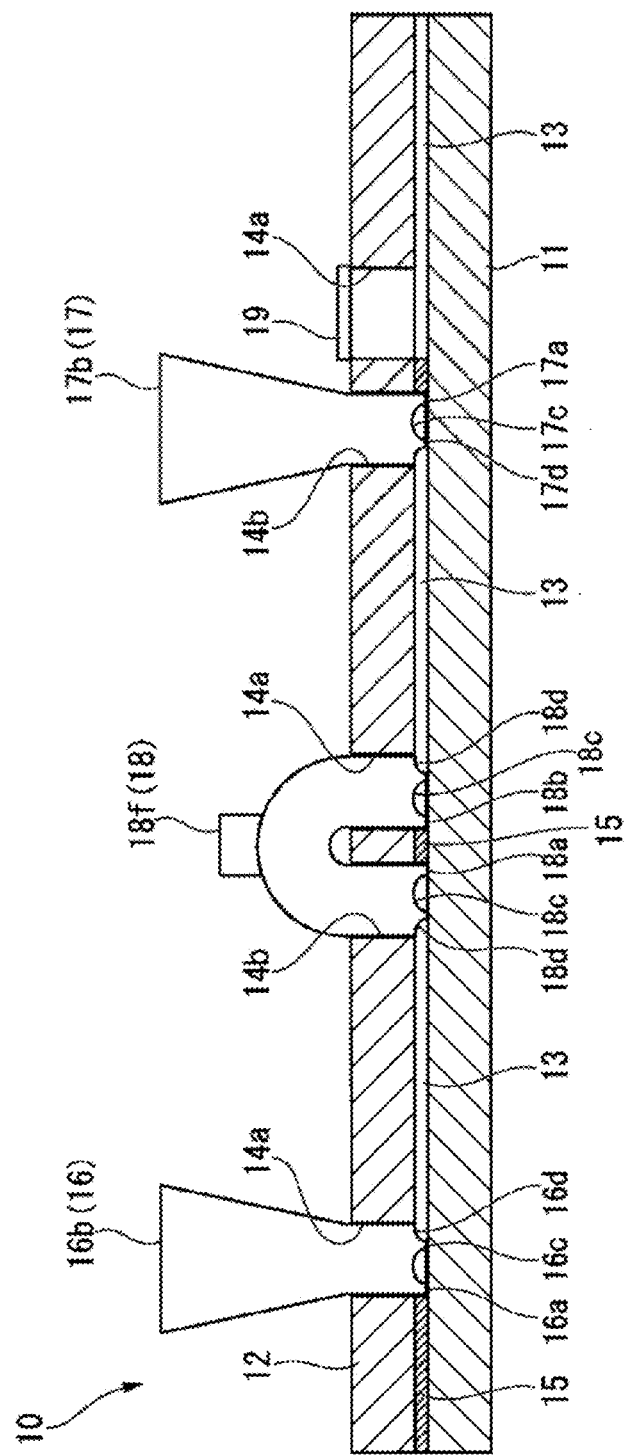
FIG. 6 is a cross-sectional view illustrating an example of a state where adapters are attached to a plate, according to an embodiment of the present invention.

FIG. 6 is a cross-sectional view illustrating an example of a state where the adapters are attached to the plate 10 of the present embodiment.

The following description is focused on the case of serially using two adjacent detection spaces 13 of the plate 10 of the present embodiment. In this case, as illustrated in FIG. 6, the adapter 16 is mounted to the port 14a of the upstream detection space 13, and the adapter 17 is mounted to the port 14b of the downstream detection space 13. The adapter 18 is mounted to the port 14b of the upstream detection space 13 and to the port 14a of the downstream detection space 13.

These adjacent detection spaces 13 are separated from each other by the adhesive layer 15, but are in communication through the adapter 18, so that a series of processes can be continuously performed.

Figure 7:
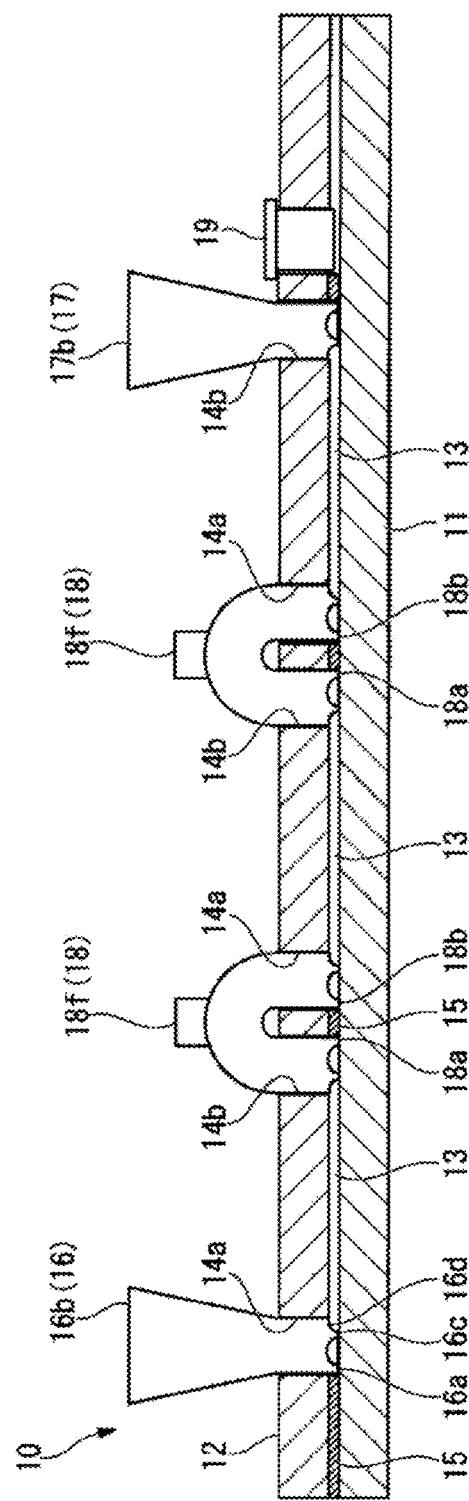
FIG. 7 is a cross-sectional view illustrating an example of a state where adapters are attached to a plate according to an embodiment of the present invention.

The ports 14a and 14b to which no adapters 16 to 18 are mounted remain sealed without the films 19 being cut through FIG. 7 is a cross-sectional view illustrating an example of a state where the adapters are attached to the plate 10 of the present embodiment.

The following description is focused on the case of serially using three adjacent detection spaces 13 of the plate 10 of the present embodiment. In this case, as illustrated in FIG. 7, the adapter 16 is mounted to the port 14a of the upstream detection space 13, and the end 18a of the adapter 18 is mounted to the port 14b of this upstream detection space 13. The end 18b of the adapter 18 is mounted to the port 14a of the detection space 13 at the intermediate position, and the end 18a of a second adapter 18 is mounted to the port 14b of the detection space 13 at the intermediate position. The end 18b of the second adapter 18 is mounted to the port 14a of the downstream detection space 13, and the adapter 17 is mounted to the port 14b of the downstream detection space 13.

As illustrated in FIGS. 5 to 7, in the plate 10 of the present embodiment, the adapter 16, the adapter 17, or the adapter 18 is attached to the ports 14a and 14b, when a liquid-containing substance is introduced into the detection space 13, and these adapters 16, 17 and 18 are detached to use the plate 10 in a thin and flat form, for reaction or detection purposes. The plate 10 may be used without detaching the adapters 16, 17 and 18.

The plate 10 of the present embodiment 10 includes: the port 14a through which a liquid-containing substance is introduced into the detection space 13; the port 14b through which a liquid-containing substance or a gas is discharged from the detection space 13; and the adapters 16 and 17 which can be attached to and detached from the ports 14a and 14b. Thus, with the adapters 16 and 17 being detached, the upper surface of the plate 10, that is, the front surface of the substrate 12, can be made flat, and also the thickness of the plate 10 is reduced, enabling heating of the plate 10 from either side thereof.

The plate 10 enables heating of the detection space 13. When the adapters 16 and 17 are detached, parts other than the detection space 13 to be used for reaction or detection are absent from the plate 10. Thus, the front surface of the plate 10 becomes flat, which prevents unwanted spread of heat in the longitudinal or lateral in-plane direction horizontal to the front surface of the plate 10. As a result, heat treatment that is uniform in the in-plane direction of the plate 10 can be performed.

Specifically, in the present embodiment, when the two substrates 11 and 12 constituting the plate 10, and a substance in the detection space 13 sandwiched between these substrates are heated, the detection space 13 can be easily uniformly heated.

Furthermore, since the front surface of the plate 10 is flat, when the interior of the detection space 13 is observed, or when fluorescence, luminescence, etc., therein is detected using a microscope or the like with a lens of a short focal length, the microscope can make an approach from one or both of the upper and lower surfaces of the plate 10.

To perform reaction and detection in the plate 10, the plate 10 needs to be of a size enabling entry of a device for reaction and detection into the plate 10. Therefore, the size of the plate 10 is limited by the device. The plate 10 of the present embodiment, however, can be designed with particularly no vertical (height direction) limitation in shape by the size of the adapters 16, 17 and 18, because the adapters 16, 17 and 18 are detachable. With this configuration, the plate 10 can include a processing mechanism for an in vivo substance, or accept a detection system producing a large amount of effluent. Note the front surface of the plate 10 may have small protrusions or the like, such as the lid portions 19b, unless the advantageous effects described above are deteriorated.

In the plate 10 of the present embodiment, a plurality of detection spaces 13 can be connected by attaching the adapter 18. Thus, the volume necessary for the reaction can be provided by setting the number of detection spaces 13 to be connected. As a result, when all the amount of the sample is desired to be used for the reaction, the sample can be used without being discarded.

Furthermore, there are a number of micropores in the detection space 13, and when molecules, cells, and other materials in the sample are put in the micropores for counting, or when a target substance in the sample is quantified, the number of micropores as a modulus can be easily increased for detection.

The adapter 18 not only connects the plurality of detection spaces 13, but also exerts other functions. Examples are as follows.

A porous member such as a filter, a semipermeable film, or the like may be provided inside (in the tube of) the adapter 18 so that substances, such as impurities or reaction products, not necessary for detection and reaction may be removed from the solution passing through the adapter 18.

The adapter 18 may be configured to include (encapsulate) a pH adjuster, or a reagent or the like different from that in the adapter 16 so that the properties of the solution are adjusted when the solution passes through the adapter 18. The adapter 18 may be configured to include a dye or the like so that the properties of the solution can be detected.

Examples of the reagent or the like include pH adjusters, buffer solutions (buffers), nucleic acids (including artificial nucleic acids), proteins, enzymes, surfactants, antibodies, supports (carriers) such as beads, color reagents (the "color" includes colors of not only the visible light range, but also colors in the range of electromagnetic waves such as ultraviolet rays, infrared rays, and the like) such as labeling reagents and dyes, and combinations of these elements (for example, a bead with an antibody, or a nucleic acid with a label).

A liquid reservoir may be provided inside the adapter 18 so that these reagents can be placed in a liquid or solid form. Furthermore, a porous member may be placed inside the adapter 18 and soak the porous member with the aforementioned reagent or the like.

The adapter 18 may be configured so that a cross-sectional shape thereof is partially or continuously changed to change the cross-sectional area of the adapter 18. Specifically, the cross-sectional shape (the tube diameter) of the adapter 18 is partially or continuously changed to give resistance against the delivery of a solution and to thereby adjust the delivery speed or the amount of the solution.

When a reagent is encapsulated in the adapter 18, a seal, a mark, or the like for identifying the kind of the encapsulated reagent may be provided to the outer wall of the adapter 18. The color of the adapter 18 may be used as a method of identification.

The plate of the present embodiment can be used for quantification and qualitative analyses.

The plate 10 of the present embodiment may be used for quantifying the concentration of an in vivo substance which may be any of a DNA, RNA, miRNA, mRNA, and protein.

<Modification 1>

A modification of the plate 10 of the present embodiment will be described below.

In the plate 10 of the present modification, a reagent suitable for an in vivo substance desired to be detected can be placed in the adapter 16. Thus, adapters 16 can be attached to the plate 10 for a plurality of detection spaces 13, according to the in vivo substances desired to be detected. Therefore, the plate 10 of the present embodiment can be used when one item is detected from among several samples or when several items are detected from one sample, as optionally selected by the user.

Furthermore, even when the reagent needs to be stored under special conditions, such as in a frozen or cooled state, only the adapter 16 needs to be stored in that state; there is no need to store the plate 10 in that state.

The reagent to be used in the plate 10 may be encapsulated in the adapter 16.

As an encapsulation method, the reagent may be thermally dried or freeze-dried for fixation to the inner wall of the adapter 16. Alternatively, the reagent in a liquid form may be encapsulated in the end 16b of the adapter 16 using a film that can be cut through.

Furthermore, when the reagent is encapsulated in the adapter 16, a seal, a mark, or the like for identifying the kind of the encapsulated reagent may be provided to the outer wall of the adapter 16. The color of the adapter 16 may be used as a method of identification.

The reagent to be encapsulated may be, for example, one used for a reaction, such as nucleic acid amplification or nucleic acid detection, or may be a fluorescent material, a buffer solution, microbeads, or the like.

When a plurality of detection spaces 13 are used, respective adapters 16 containing different reagents suitable for the in vivo substances desired to be detected may be mounted to the plurality of detection spaces 13 so that a plurality of targets to be detected are simultaneously detected. In this case, the adapters 16 containing the same reagent may be mounted so that a plurality of samples are simultaneously detected.

<Modification 2>

A Modification 2 of the plate 10 according to the present embodiment will be described below.

In the plate 10 of the present modification, the end 17b of the adapter 17 is not open, but closed. At the closed end, for example, there may be an effluent reservoir which is provided with a sponge 17e for absorbing the effluent.

In this case, the lower end of the sponge 17e is designed to be located at a position not contacting the sample after the sponge 17e has absorbed the effluent.

With the end 17b of the adapter 17 being closed, the end 17b is rendered to be flexible, elastic, and restorable. Thus, for example, the effluent in the detection space 13 can be sucked when the end 17b of the adapter 17 restores its shape with elasticity after being pinched and compressed. In this case, for example, the closed end 17b may be provided with only an effluent reservoir, or may additionally be provided with the sponge 17e that absorbs the effluent. In this case, the effluent can be discharged without being released externally.

Furthermore, a small hole may be formed in the closed end 17b of the adapter 17, so that a solution such as a reagent in the detection space 13 or the adapters 16, 17, and 18 are moved by deforming the adapter 17, with the small hole of the closed end 17b being pressed with a finger or the like.

Other than this, an adapter 17 having a closed end 17b, or an adapter 17 having an end 17b with a small hole may also be used to remove air bubbles contained in the reagent or the like in each adapter or each detection space 13.

Figure 8:
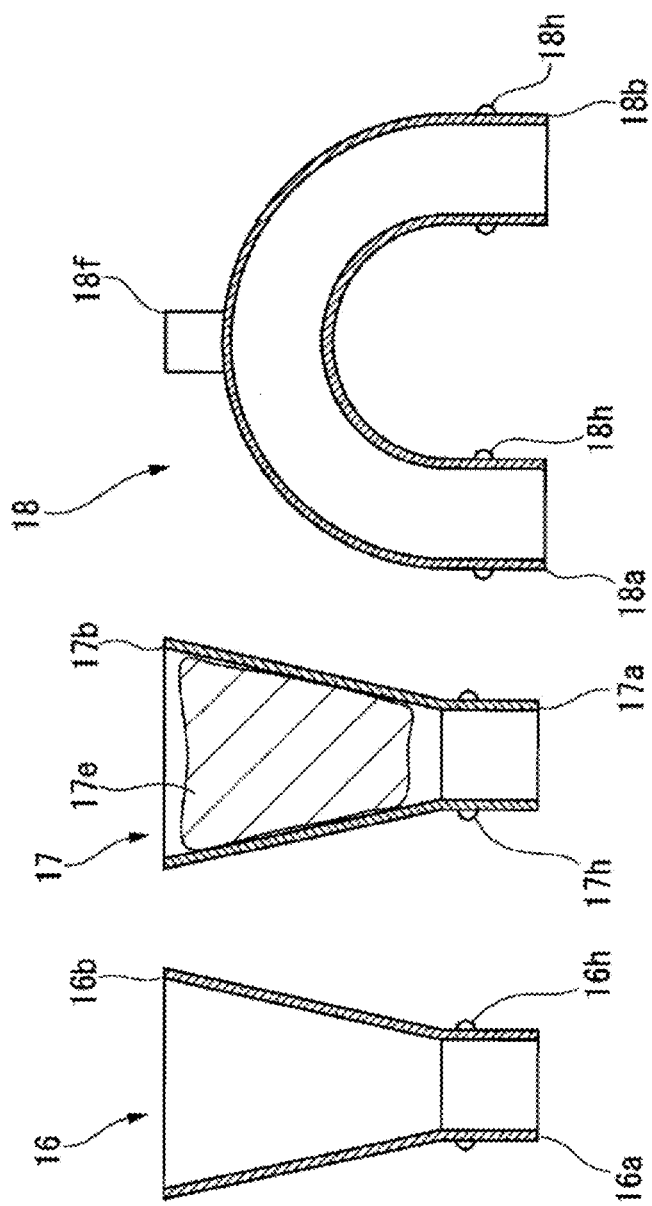
FIG. 8 is a front cross-sectional view illustrating another example of adapters of a plate, according to an embodiment of the present invention.

FIG. 8 is a front cross-sectional view illustrating another example of the adapters of the present embodiment.

In the embodiment described above, the abutment portions 16c and 17c and the cutout portions 16d and 17d are provided at the ends 16a and 17a of the adapters 16 and 17 to secure a flow path. Other than this, protrusion portions 16h and 17h may be provided to the outer peripheral positions of the ends 16a and 17a to provide a flow path securing portion. The flow path securing portion can determine the insertion depth of the ends 16a and 17a so that they do not abut against the front surface of the substrate 11 when fitted to the respective ports.

The protrusion portions 16h and 17h may be provided to the outer peripheries of the ends 16a and 17a as continuous ridges. Alternatively, as illustrated in FIG. 8, the protrusion portions 16h and 17h may be provided as intermittent ridges, or may be provided to the peripheries of the ends 16a and 17a, for example, as protrusions located at one or more positions, preferably two or more positions.

By providing these protrusion portions 16h and 17h so as to be located on the front surface of the substrate 12, fitting depth is determined so that the ends 16a and 17b do not abut against the substrate 11.

As illustrated in FIG. 8, at least one of the one ends 18a and 18b of the adapter 18 may be similarly provided with a protrusion portion 18h. In the adapter 18, the protrusion portion 18h may be provided on the outer peripheries of both the ends 18a and 18b, or may be provided on the outer periphery of only one of the ends 18a and 18b.

Figure 9:
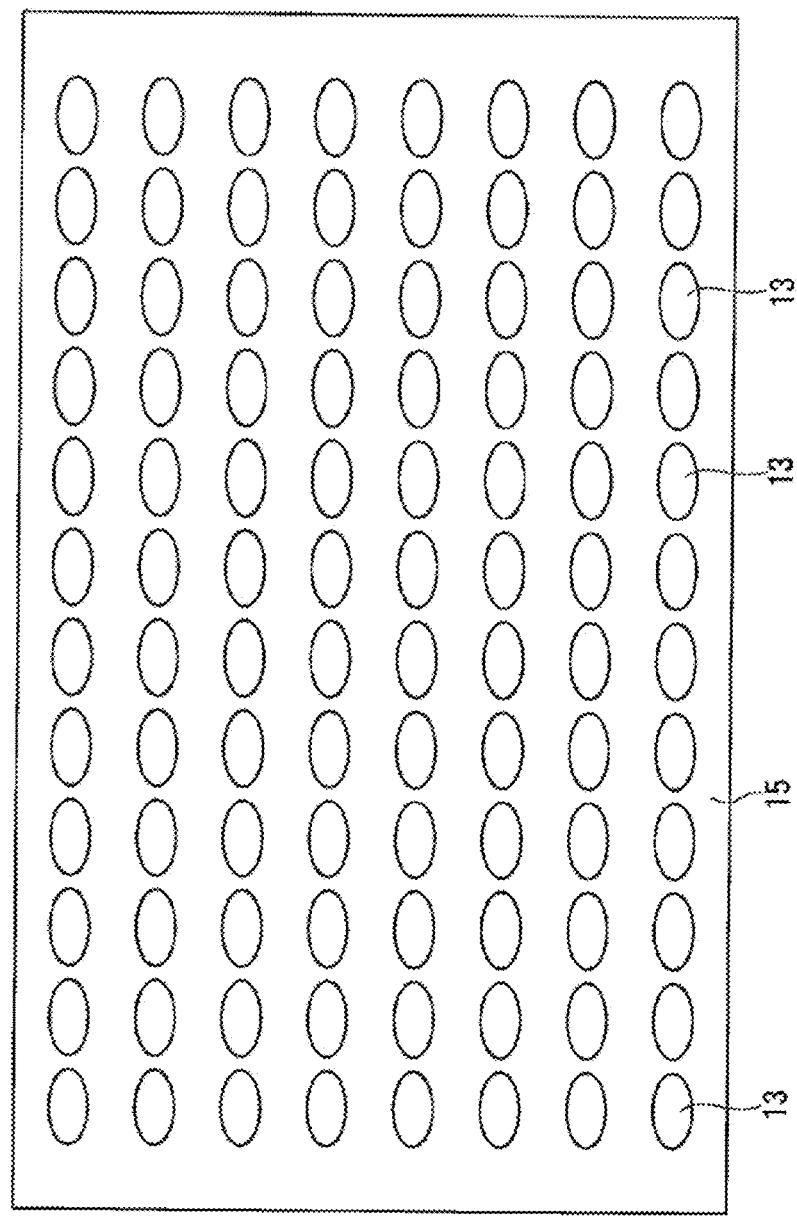
FIG. 9 is a schematic plan view illustrating another example of a plate, according to an embodiment of the present invention.

As illustrated in FIG. 9, the detection space 13 serving as a flow path may have a thickness, that is, a width orthogonal to the direction of the flow path, with a size, large or small, necessary for a predetermined reaction. FIG. 9 illustrates only the adhesive layer 15 part to show the shape of the detection space 13.

EXAMPLES

Some examples of the present invention will be described below.

<Example 1 Using Adapters 16 and 17>

A glass wafer with a thickness of 0.5 mm was spin-coated with a fluorine-based resin (CYTOP manufactured by Asahi Glass Co., Ltd) and cured at 180° C. for 3 hours. Subsequently, the resultant object was exposed using a photomask, followed by dry-etching, thereby preparing a substrate 11 having a fluorine-based resin coating which is formed with 1,000,000 pores with a diameter of 5 to 6 μm and a depth of 3 μm.

A transparent film formed with through holes (ports) with a diameter of 2 mm serving as a substrate 12 was bonded to the substrate 11 using a double-sided tape as an adhesive layer 15 with a thickness of 100 thereby forming a plate 10.

An invader reaction reagent was prepared, containing 1 μM probe, 1 μM Invader oligo, 2 μM FRET cassette, 10 mM MOPS buffer solution, and 500 U/μl Cleavase. This reagent was dispensed to the inner wall of an adapter 16 formed of a resin, followed by drying and fixation for 15 minutes using an oven set to 60° C.

The adapter 16 with the dried and fixed reagent was attached to a through hole (port) 14a of a plate, and an adapter 17 formed of a resin was attached to another through hole (port) 14b of the plate.

As a sample, a solution was prepared by mixing an artificially synthesized DNA with 10 mM magnesium chloride and 0.05% of a surfactant. The artificially synthesized DNA was designed to have the same sequence as the target gene sequence of the invader reaction reagent. This sample was delivered through the adapter 16 together with the reagent dried and fixed onto the inner wall of the adapter 16, so that the detection space 13 of the plate 10 was filled with the liquid.

Then, a hydrophobic fluorine-based liquid (FC40) was delivered through the adapter 16 to replace the reagent in the detection space 13 of the plate 10 with the fluorine-based liquid, except for the reagent in the micropores.

The adapters 16 and 17 were detached, and the through holes (ports) 14a and 14b were sealed with adhesive films, followed by warming the plate 10 up to 63° C. using a hot plate, and then left for 15 minutes for reaction.

The reaction in the micropores of the detection space 13 of the plate 10 was detected using a fluorescence microscope from both the upper side (the substrate 12 side) and the lower side (the substrate 11 side) of the plate 10.

Figure 10:
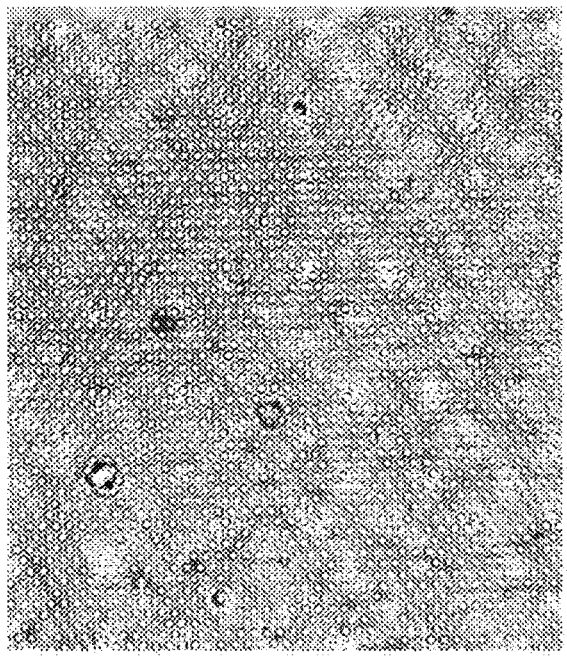
FIG. 10 is an image showing an experiment performed using a plate according to an embodiment of the present invention.
Figure 11:
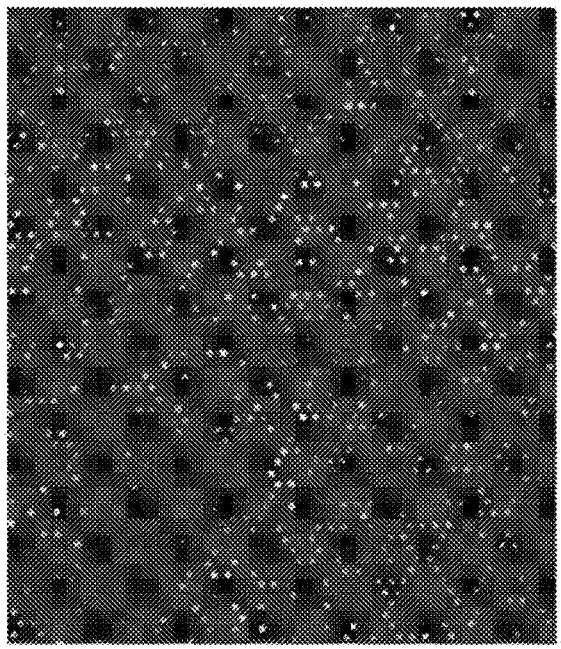
FIG. 11 is an image showing an experiment performed using a plate according to an embodiment of the present invention.
Figure 12:
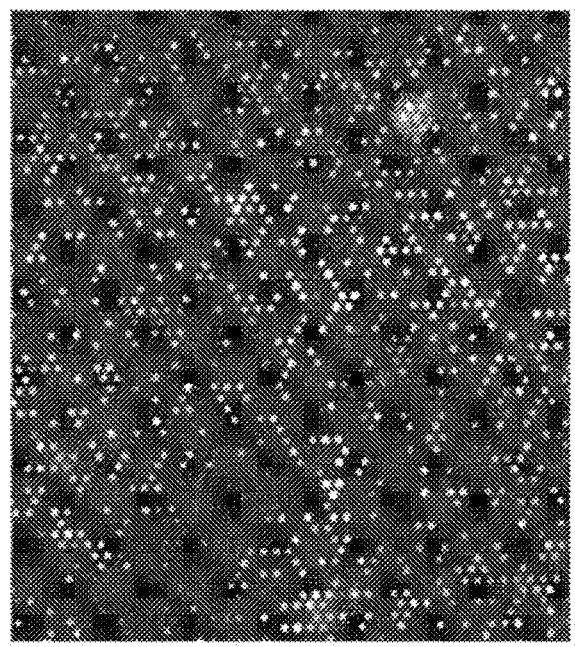
FIG. 12 is an image showing an experiment performed using a plate according to an embodiment of the present invention.
Figure 13:
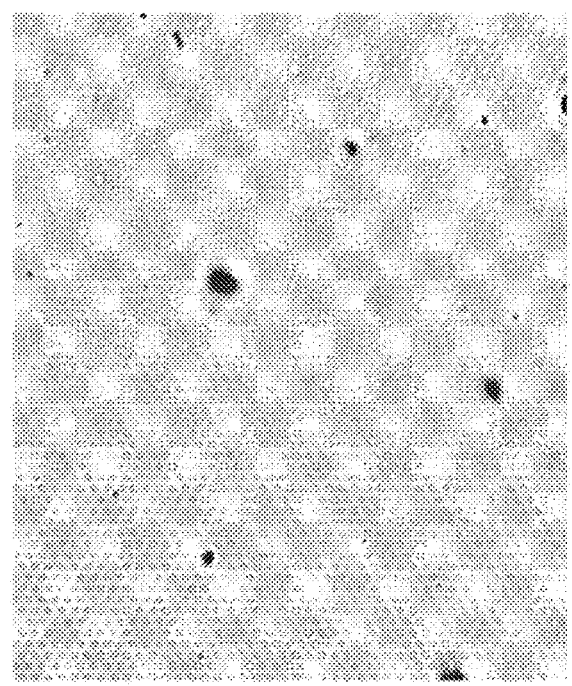
FIG. 13 is an image showing an experiment performed using a plate according to an embodiment of the present invention.
Figure 14:
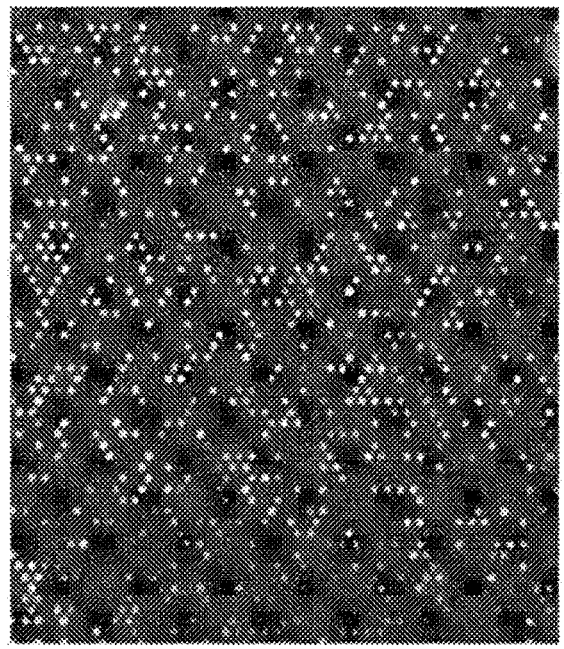
FIG. 14 is an image showing an experiment performed using a plate according to an embodiment of the present invention.
Figure 15:
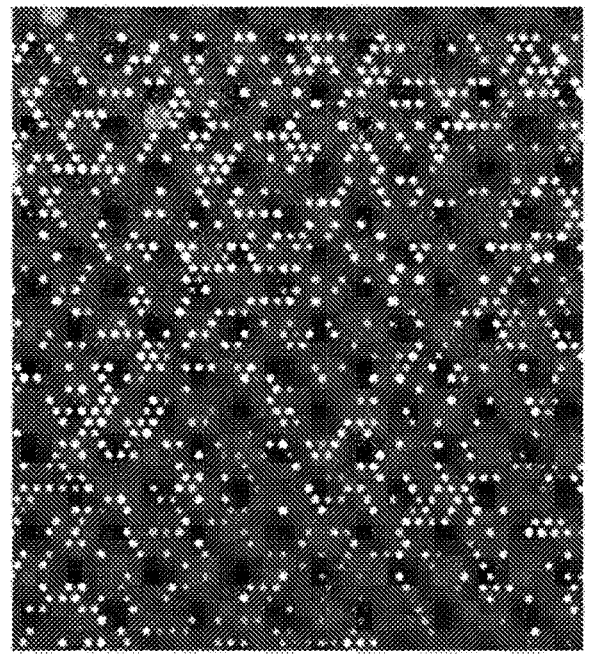
FIG. 15 is an image showing an experiment performed using a plate according to an embodiment of the present invention.

FIG. 10 is a bright-field image observed from the upper side. FIG. 11 is a detection image of fluorescence 1 observed from the upper side. FIG. 12 is a detection image of fluorescence 2 observed from the upper side. FIG. 13 is a bright-field image observed from the lower side. FIG. 14 is a detection image of the fluorescence 1 observed from the lower side. FIG. 15 is a detection image of the fluorescence 2 observed from the lower side. It was confirmed that the micropores in the space of the plate could be observed from both sides, and the reaction occurring inside the micropores could be detected from both sides.

Note that the fluorescence 1 and the fluorescence 2 have different detection wavelengths.

<Example 2 Using Adapter 18 to Connect Two Spaces 13>

A glass wafer with a thickness of 0.5 mm was spin-coated with fluorine-based resin (CYTOP manufactured by Asahi Glass Co., Ltd) and cured at 180° C. for 3 hours. Subsequently, the resultant object was exposed using a photomask, followed by dry-etching, thereby preparing a substrate 11 having a fluorine-based resin coating which is formed with 1,000,000 pores with a diameter of 5 to 6 μm and a depth of 3 μm.

A transparent film formed with through holes (ports) with a diameter of 2 mm serving as a substrate 12 was bonded to the substrate 11 using a double-sided tape as an adhesive layer 15 with a thickness of 100 thereby forming a plate 10 including two detection spaces 13.

An invader reaction reagent was prepared, containing 1 μM probe, 1 μM Invader oligo, 2 μM FRET cassette, 10 mM MOPS buffer solution, and 500 U/μl Cleavase. This reagent was dispensed to the inner wall of an adapter 16 formed of a resin, followed by drying and fixation for 15 minutes using an oven set to 60° C.

The adapter 16 with the dried and fixed reagent was attached to the through hole (port) 14a of the first detection space 13 of the plate. An adapter 18 made of silicone was attached to another through hole (port) 14b and to the through hole (port) 14a of the second detection space 13. In this way, the two detection spaces were connected, and an adapter 17 formed of a resin was attached to the through hole (port) 14b of the second detection space 13.

As a sample, a solution was prepared by mixing an artificially synthesized DNA with 10 mM magnesium chloride and 0.05% of a surfactant. The artificially synthesized DNA was designed to have the same sequence as the target gene sequence of the invader reaction reagent. This sample was delivered through the adapter 16 together with the reagent dried and fixed onto the inner wall of the adapter 16. Thus, the first detection space 13 of the plate 10 was filled with the liquid.

Then, a hydrophobic fluorine-based liquid (FC40) was delivered through the adapter 16 to replace the reagent on the outside of the micropores of the first detection space 13 with the fluorine-based liquid. Along with this, the second detection space 13 was filled with the reagent solution expelled from the first detection space 13 through the adapter 18. Subsequently, the reagent on the outside of the micropores of the second detection space 13 was replaced with the fluorine-based liquid expelled from the first detection space 13.

The adapters 16, 17 and 18 were detached, and the through holes (ports) 14a and 14b were sealed with adhesive films, followed by warming the plate 10 up to 63° C. using a hot plate, and then left for 15-minute reaction.

The reaction in the micropores of the detection space 13 of the plate 10 was detected not only for the first detection space 13, but also for the second detection space 13.

Figure 16:
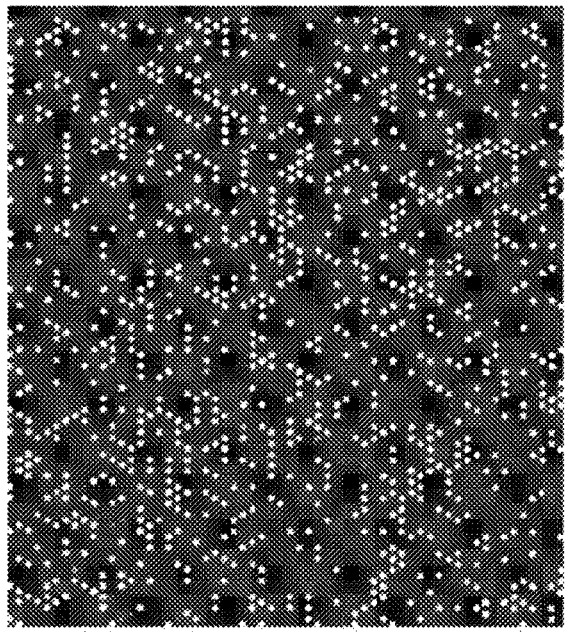
FIG. 16 is an image showing an experiment performed using a plate according to an embodiment of the present invention.
Figure 17:
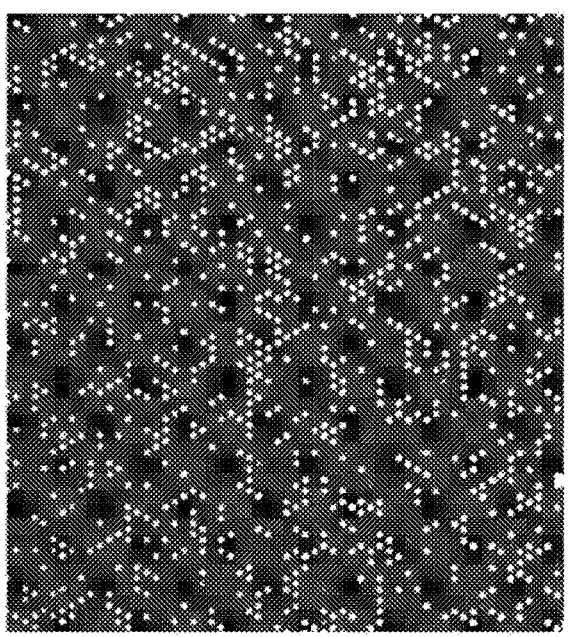
FIG. 17 is an image showing an experiment performed using a plate according to an embodiment of the present invention.

FIG. 16 is a detection image of fluorescence 1 observed from above the substrate 12 of the first detection space 13. FIG. 17 is a detection image of fluorescence 1 observed from above the substrate 12 of the second detection space 13. It was confirmed that as a result of these detection spaces being connected with the adapter 18, the reagent solution could be encapsulated in the micropores of the second detection space, and a reaction could be observed, which was similar to the reaction inside the micropores observed in the first detection space.

<Example 3 for Continuously Performing Different Processes in Reagent-Containing Adapter 16, Adapter 18 and Different Spaces 13>

Verification was conducted for a method of detecting a target nucleic acid in a nucleic acid solution by removing beads from a nucleic acid solution sample that contains the beads. Specifically, the beads were removed from the reagent in the first detection space 13, and the reagent was caused to react in the second detection space 13.

A glass wafer having a thickness of 0.5 mm was spin-coated with a fluorine-based resin (CYTOP manufactured by Asahi Glass Co., Ltd) and cured at 180° C. for 3 hours. Subsequently, the resultant object was exposed using a photomask, followed by dry-etching, thereby preparing a substrate 11 having a fluorine-based resin coating which is formed with 1,000,000 pores with a diameter of 5 to 6 μm and a depth of 3 μm.

A transparent film formed with through holes (ports) with a diameter of 2 mm serving as a substrate 12 was bonded to the substrate 11 using a double-sided tape as an adhesive layer 15 with a thickness of 100 thereby forming a plate 10 including two detection spaces 13.

An invader reaction reagent was prepared, containing 1 μM probe, 1 μM Invader oligo, 2 μM FRET cassette, 10 mM MOPS buffer solution, and 500 U/μl Cleavase. This reagent was dispensed to the inner wall of an adapter 16 formed of a resin, followed by drying and fixation for 15 minutes using an oven set to 60° C.

The adapter 16 with the dried and fixed reagent was attached to the through hole (port) 14a of the first detection space 13 of the plate. An adapter 18 made of silicone was attached to another through hole 14b and the through hole (port) 14a of the second detection space 13. In this way, the two detection spaces were connected, and an adapter 17 formed of a resin was attached to the through hole (port) 14b of the second detection space 13.

As a sample, a solution was prepared by mixing an artificially synthesized DNA with 10 mM magnesium chloride, 0.05% of a surfactant, and beads having a diameter of 3 μm. The artificially synthesized DNA was designed to have the same sequence as the target gene sequence of the invader reaction reagent. The sample was delivered through the adapter 16 together with the reagent dried and fixed onto the inner wall of the adapter 16. Thus, the first detection space 13 of the plate 10 was filled with the liquid.

The plate 10 was centrifuged using a plate centrifuge. Subsequently, a fluorine-based liquid was delivered through the adapter 16 and, while the beads were trapped by the micropores of the first detection space 13, the reagent excepting the beads was replaced with the fluorine-based liquid. Along with this, the second detection space 13 was filled with the reagent solution expelled from the first detection space 13 through the adapter 18. Subsequently, the reagent on the outside of the micropores of the second detection space 13 was replaced with the fluorine-based liquid expelled from the first detection space 13.

The adapters 16, 17 and 18 were detached, and the through holes (ports) 14a and 14b were sealed with adhesive films, followed by warming the plate 10 up to 63° C. using a hot plate, and then left for 15-minute reaction.

The beads in the first detection space 13 of the plate 10 were observed, and the reaction in the micropores of the second detection space 13 was detected.

Figure 18:
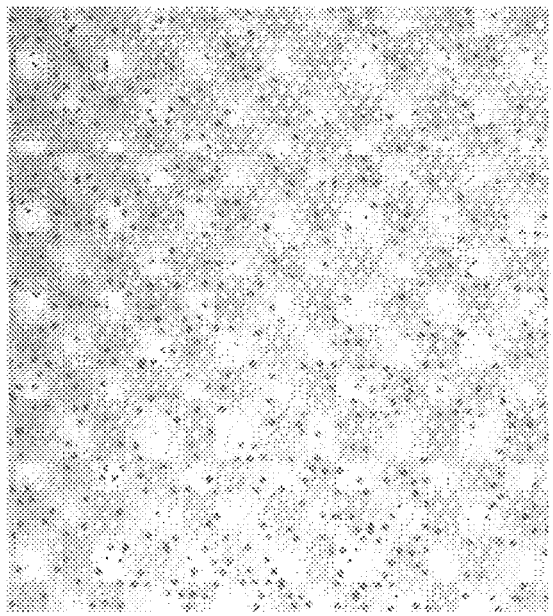
FIG. 18 is an image showing an experiment performed using a plate according to an embodiment of the present invention.
Figure 19:
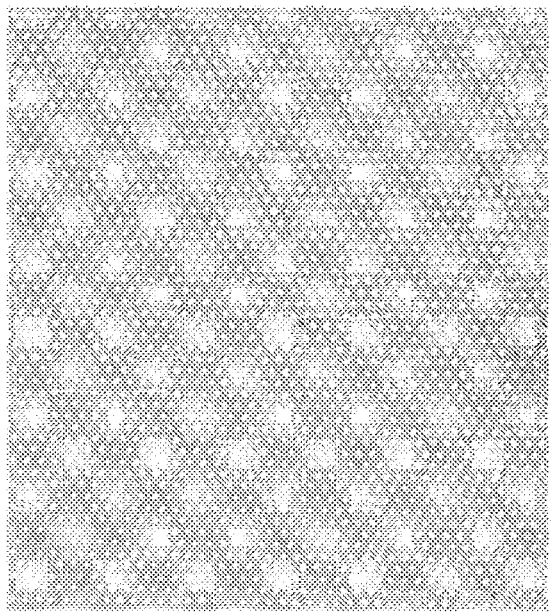
FIG. 19 is an image showing an experiment performed using a plate according to an embodiment of the present invention.
Figure 20:
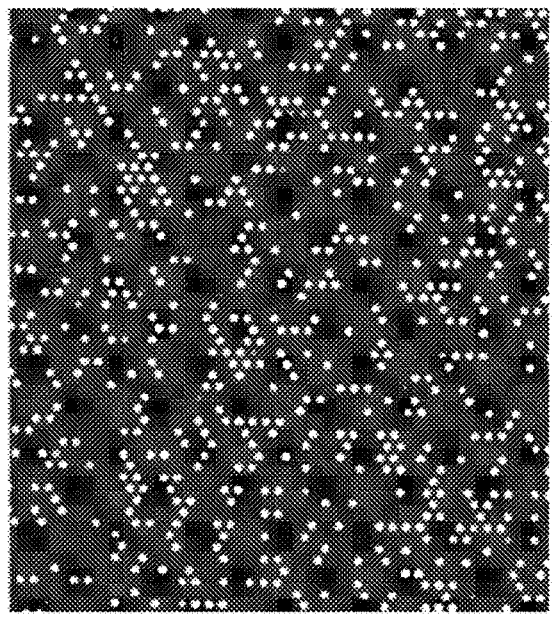
FIG. 20 is an image showing an experiment performed using a plate according to an embodiment of the present invention.

FIG. 18 is a bright-field image observed from above the substrate 12 of the first detection space 13. FIG. 19 is a bright-field image observed from above the substrate 12 of the second detection space 13. FIG. 20 is a detection image of fluorescence 1. The bright-field images of the two detection spaces 13 show that a large number of beads were observed in the micropores of the first detection space 13 and almost no beads were observed in the micropores of the second detection space 13. Thus, the beads were trapped in the first detection space 13, and the reagent solution removed with the beads was introduced into the second detection space 13. Furthermore, the reaction of the reagent solution removed with the beads, occurring in the micropores of the second detection space, was confirmed by way of detection of fluorescence.

<Example 4 for Simultaneously Performing Different Processes in Different Spaces 13 Using Adapters 16 Provided with Different Reagents>

A glass wafer with a thickness of 0.5 mm was spin-coated with a fluorine-based resin (CYTOP manufactured by Asahi Glass Co., Ltd) and cured at 180° C. for 3 hours. Subsequently, the resultant object was exposed using a photomask, followed by dry-etching, thereby preparing a substrate 11 having a fluorine-based resin coating which is formed with 1,000,000 pores with a diameter of 5 to 6 µm and a depth of 3 µm.

A transparent film formed with through holes (ports) with a diameter of 2 mm serving as a substrate 12 was bonded to the substrate 11 using a double-sided tape as an adhesive layer 15 with a thickness of 100 thereby forming a plate 10 including two detection spaces 13.

An invader reaction reagent for detecting a mutant-type epidermal growth factor receptor (EGFR) gene was prepared, containing 1 µM probe, 1 µM Invader oligo, 2 µM FRET cassette, 10 mM MOPS buffer solution, and 500 U/µl Cleavase. This reagent was dispensed to the inner wall of a first adapter 16 formed of a resin. Furthermore, an invader reaction reagent for detecting a wild-type EGFR gene was prepared. This reagent was dispensed to the inner wall of a second adapter 16 formed of a resin. These were dried for fixation for 15 minutes using an oven set to 60° C.

The first adapter 16 with the dried and fixed reagent for detecting a mutant-type gene was attached to the through hole (port) 14a of the first detection space 13 of the plate, and a first adapter 17 formed of a resin was attached to another through hole (port) 14b of the first detection space 13 of the plate. The second adapter 16 with the dried and fixed reagent for detecting a wild-type gene was attached to the through hole (port) 14a of the second detection space 13 of the plate, and a second adapter 17 formed of a resin was attached to another through hole (port) 14b of the second detection space 13 of the plate.

As a sample, a solution was prepared by mixing an artificially synthesized DNA with 10 mM magnesium chloride and 0.05% of a surfactant. The artificially synthesized DNA was designed to have the same sequence as the mutant-type gene sequence of the invader reaction reagent. The sample was delivered through the first adapter 16 together with the reagent dried and fixed onto the inner wall of this adapter 16. Thus, the first detection space 13 of the plate 10 was filled with the liquid.

Then, a hydrophobic fluorine-based liquid (FC40) was delivered through the first adapter 16 to replace the reagent on the outside of the micropores of the first detection space 13 with the fluorine-based liquid.

As a sample, a solution was prepared by mixing an artificially synthesized DNA with 10 mM magnesium chloride and 0.05% of a surfactant. The artificially synthesized DNA was designed to have the same sequence as the wild-type gene sequence of the invader reaction reagent. The sample was delivered through the second adapter 16 together with the reagent dried and fixed onto the inner wall of this adapter 16. Thus, the second detection space 13 of the plate 10 was filled with the liquid.

Then, a hydrophobic fluorine-based liquid (FC40) was delivered through the second adapter 16 to replace the reagent on the outside of the micropores of the second detection space 13 with the fluorine-based liquid.

The first and second adapters 16 and 17 were detached, and the holes (ports) 14a and 14b of the first and second detection spaces 13 were sealed with adhesive films. Subsequently, the plate 10 was warmed up to 63° C. using a hot plate, and left for 15 minutes for reaction.

The reaction in the micropores of the two detection spaces 13 of the plate 10 was detected.

Figure 21:
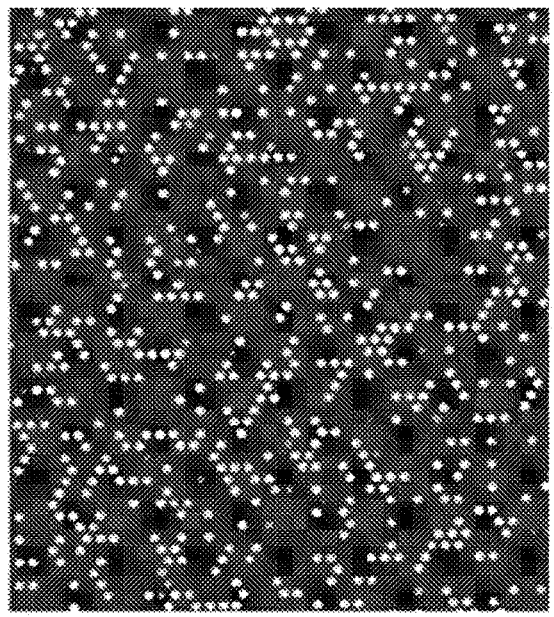
FIG. 21 is an image showing an experiment performed using a plate according to an embodiment of the present invention.
Figure 22:
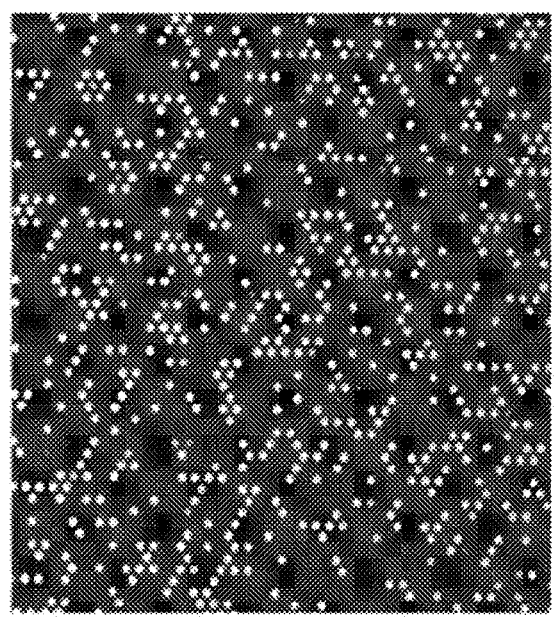
FIG. 22 is an image showing an experiment performed using a plate according to an embodiment of the present invention.

FIG. 21 is a detection image of fluorescence 1 observed from above the substrate 12 of the first detection space 13. FIG. 22 is a detection image of the fluorescence 1 observed from above the substrate 12 of the second detection space 13. It was confirmed that the mutant-type gene was detected in the first detection space 13 and the wild-type gene was detected in the second detection space 13.

<Example 5 Using No Adapter 16>

A glass wafer with a thickness of 0.5 mm was spin-coated with a fluorine-based resin (CYTOP manufactured by Asahi Glass Co., Ltd) and cured at 180° C. for 3 hours. Subsequently, the resultant object was exposed using a photomask, followed by dry-etching, thereby preparing a substrate 11 having a fluorine-based resin coating which is formed with 1,000,000 pores with a diameter of 5 to 6 µm and a depth of 3 µm.

A transparent film formed with through holes (ports) with a diameter of 2 mm serving as a substrate 12 was bonded to the substrate 11 using a double-sided tape as an adhesive layer 15 with a thickness of 100 thereby forming a plate 10.

An invader reaction reagent was prepared as a sample solution, containing 1 µM probe, 1 µM Invader oligo, 2 µM FRET cassette, 10 mM MOPS buffer solution, 500 U/µl Cleavase, an artificially synthesized DNA, 10 mM magnesium chloride, and 0.05% surfactant. The sample was delivered to the detection space 13 of the plate 10 through the through hole (port) 14a using a pipette. In the delivery, the tip of the pipette did not properly fit to the through hole (port) 14a, which, coupled with the fact that the inner wall of the detection space 13 was hydrophobic, hindered smooth entry of the sample solution into the detection space 13.

<Example 6 Using No Adapter 17>

A glass wafer with a thickness of 0.5 mm was spin-coated with a fluorine-based resin (CYTOP manufactured by Asahi Glass Co., Ltd) and cured at 180° C. for 3 hours. Subsequently, the resultant object was exposed using a photomask, followed by dry-etching, thereby preparing a substrate 11 having a fluorine-based resin coating which is formed with 1,000,000 pores with a diameter of 5 to 6 μm and a depth of 3 μm.

A transparent film formed with through holes (ports) with a diameter of 2 mm serving as a substrate 12 was bonded to the substrate 11 using a double-sided tape as an adhesive layer 15 with a thickness of 100 thereby forming a plate 10.

An invader reaction reagent was prepared, containing 1 μM probe, 1 μM Invader oligo, 2 μM FRET cassette, 10 mM MOPS buffer solution, and 500 U/μl Cleavase. This reagent was dispensed to the inner wall of an adapter 16 formed of a resin, and dried for fixation for 15 minutes using an oven set to 60° C.

The adapter 16 with the dried and fixed reagent was attached to the through hole (port) 14a of the plate. As a sample, a solution was prepared by mixing an artificially synthesized DNA with 10 mM magnesium chloride and 0.05% of a surfactant. The artificially synthesized DNA was designed to have the same sequence as the target gene sequence of the invader reaction reagent. In the state where nothing was attached to the through hole (port) 14b, this sample was delivered through the adapter 16 together with the reagent dried and fixed onto the inner wall of the adapter 16 to fill the detection space 13 of the plate 10 with the liquid.

Then, a hydrophobic fluorine-based liquid (FC40) was delivered through the adapter 16 to replace the reagent on the outside of the micropores of the first detection space 13 of the plate 10 with the fluorine-based liquid.

The replacement caused a problem that the reagent solution and the fluorine-based liquid overflowed from the through hole (port) 14b and adhered to the side surfaces of the plate 10 or the outer side surface of the detection space 13.

Observation of a sample involves use of a microscope or the like. However, such an optical system has a short focal length, and therefore the distance between the sample and the optical device is limited to a short range. Thus, there is a need for reducing the thickness of a sample or parts surrounding the sample. When the thickness of a sample is reduced, it is difficult to inject a sample into a detection region. Thus, there have not been established easy and reliable approaches for sample observation.

The present invention has an aspect to provide a highly versatile and practical plate including an adapter that can be customized by a user when detecting an in vivo substance. Furthermore, the present invention has another aspect to provide a method of using the plate.

A plate according to an aspect of the present invention includes: a first substrate having a front surface and a back surface; a second substrate facing the back surface of the first substrate to form a detection space detectable from outside, the detection space being formed between the second substrate and the back surface of the first substrate; a first port provided to the front surface of the first substrate and having a through hole communicating with the detection space to deliver a liquid-containing substance into the detection space; a second port provided to the front surface of the first substrate and having a through hole communicating with the detection space to discharge a liquid-containing substance or a gas from the detection space; and an adapter attachable to and detachable from the first port and the second port. In the plate, the adapter is configured to be attached when liquid is delivered to or discharged from the detection space, and to be detached when the interior of the detection space is observed from outside, and in a state where the adapter is detached, the front surface of the first substrate is flat.

In the aspect described above, the adapter may be a tube permitting the detection space to communicate externally and having a first end that can be fitted to the through hole, and a second end that is an open end with a larger diameter than the first end.

In the aspect described above, the adapter may permit the detection space to communicate with the other detection space, and may have a first end that can be fitted to the through hole of the detection space, and a second end that can be fitted to the through hole of the other detection space.

In the aspect described above, the adapter may have an inner wall to which a reagent is fixed, the adapter being configured to deliver the reagent into the detection space.

In the aspect described above, the adapter may be configured to discharge the substance from the detection space, and has a first end that can be fitted to the through hole and a second end that is an open end or a closed end with a larger diameter than the first end.

In the aspect described above, the adapter may be configured to discharge the substance from the detection space, and may have a first end that can be fitted to the through hole and a second end that is an open end or a closed end with a larger diameter than the first end.

In the aspect described above, the adapter may be provided therein with an absorbing means for absorbing an effluent, and may be configured to absorb an effluent discharged from the detection space.

In the aspect described above, at least one of the first substrate and the second substrate may be configured to have transparency to enable detection of fluorescence or luminescence in the detection space from outside.

In the aspect described above, both the first substrate and the second substrate may be configured to have transparency to enable detection of fluorescence or luminescence in the detection space from outside.

In the aspect described above, the plate may be provided with a plurality of the detection spaces, with the adapter being configured to establish communication between the plurality of the detection spaces.

In the aspect described above, in the detection space, at least one of the first substrate and the second substrate may have a surface provided with one or more pores with a capacity of 1 pl or less.

In the aspect described above, the plate may be configured to quantify a concentration of an in vivo substance.

In the aspect described above, the in vivo substance may be any of DNA, RNA, miRNA, mRNA, and a protein.

In the aspect described above, the through hole may be covered with a film or lid that can be detached or cut through.

In the aspect described above, the detection space may be configured to be heated.

A plate according to an aspect of the present invention includes: a first substrate having a front surface and a back surface; a second substrate facing the back surface of the first substrate to form a detection space detectable from outside, the detection space being formed between the second substrate and the back surface of the first substrate; a first port provided to the front surface of the first substrate and having a through hole communicating with the detection space to deliver a liquid-containing substance into the detection space; a second port provided to the front surface of the first substrate and having a through hole communicating with the detection space to discharge a liquid-containing substance or a gas from the detection space; and an adapter attachable to and detachable from the first port and the second port. In the plate, the adapter is configured to be attached when liquid is delivered to or discharged from the detection space, and to be detached when the interior of the detection space is observed from outside, and in a state where the adapter is detached, the front surface of the first substrate is flat. Thus, when the adapter is made thin and observed being magnified by an optical device such as a microscope, the observation distance can be shortened up to a focal length range suitable for the magnification ratio required for the observation. At the same time, the necessary amount of the reagent, sample, or the like can be reduced, enabling reliable reaction and detection with an amount than smaller in the conventional art.

In the aspect described above, the adapter may be a tube permitting the detection space to communicate externally and having a first end that can be fitted to the through hole, and a second end that is an open end with a larger diameter than the first end. With this configuration, the sample or reagent can be suitably injected into the adapter when the sample or reagent is used with an amount smaller than in the conventional art. Furthermore, the head of an optical system can be brought close to the aforementioned focal length range.

In the aspect described above, the adapter may permit the detection space to communicate with the other detection space, and may have a first end that can be fitted to the through hole of the detection space, and a second end that can be fitted to the through hole of the other detection space. This enables performing continuous and sequential different processes in a plurality of detection spaces connected in series, or can increase the amount of a sample processed simultaneously by establishing communication between the plurality of detection spaces. Furthermore, the time taken for the sample to pass through the detection spaces can be increased to secure the time required for the necessary reaction or the like. Thus, advantageous effects due to the detection spaces being connected can be exerted.

In the aspect described above, the adapter may have an inner wall to which a reagent is fixed, the adapter being configured to deliver the reagent into the detection space. Thus, the reagent for a desired reaction can be used easily and conveniently, and handleability of the reagent is improved. Furthermore, a specific reaction can be selected for processing.

In the aspect described above, the adapter may be configured to discharge the substance from the detection space, and may have a first end that can be fitted to the through hole and a second end that is an open end or a closed end with a larger diameter than the first end. This facilitates absorption/suction and storage of a substance when discharged from the detection space. Furthermore, the substance can be discharged from the detection space without releasing materials externally.

In the aspect described above, the adapter may be provided therein with an absorbing means for absorbing an effluent, and may be configured to absorb an effluent discharged from the detection space. This facilitates absorption/suction and storage of the effluent or the like when discharged from the detection space. Furthermore, the effluent or the like can be discharged from the detection space without releasing materials externally, by only detaching the adaptor after absorption of the effluent.

In the aspect described above, at least one of the first substrate and the second substrate may be configured to have transparency to enable detection of fluorescence or luminescence in the detection space from outside. With this configuration, the head of an optical system can be brought close to the aforementioned focal length range.

In the aspect described above, both the first substrate and the second substrate may be configured to have transparency to enable detection of fluorescence or luminescence in the detection space from outside. With this configuration, the head of an optical system can be brought close to the aforementioned focal length range from both sides of the plate.

In the aspect described above, the plate may be provided with a plurality of the detection spaces, with the adapter being configured to establish communication between the plurality of the detection spaces. This enables performing continuous and sequential different processes in a plurality of detection spaces connected in series, or can increase the amount of a sample processed simultaneously by establishing communication between the plurality of detection spaces. Furthermore, the time taken for the sample to pass through the detection spaces can be increased to secure the time required for the necessary reaction or the like. In addition, advantageous effects due to the detection spaces being connected, such as control of processing time due to the setting of continuous stages, can be exerted.

In the aspect described above, in the detection space, at least one of the first substrate and the second substrate may have a surface provided with one or more pores with a capacity of 1 pl or less. Thus, the plate can be applied to, for example, a biological substance inspection that involves a reaction, such as an enzyme reaction, in a very small space with a very small volume.

In the aspect described above, the plate may be configured to quantify a concentration of an in vivo substance. Thus, the plate can be applied to PCR or the like.

In the aspect described above, the in vivo substance may be any of DNA, RNA, miRNA, mRNA, and a protein.

In the aspect described above, the through hole may be covered with a film or lid that can be detached or cut through.

In the aspect described above, the detection space may be configured to be heated.

The plate according to the aforementioned aspect of the present invention includes an adapter that can be customized by the user, and thus has high versatility and practicality. The present invention can be used for biological substance inspection, such as PCR amplification and nucleic acid detection reaction, in which nucleic acid in a sample is quantified by detecting a signal, such as fluorescence, and calculating the percentage of microdroplets from which the signal has been detected among the total number of microdroplets. Thus, the present invention can provide a plate that is favorably reduced in thickness and volume.

INDUSTRIAL APPLICABILITY

For example, the present invention can be used for high-sensitive detection or quantification of an in vivo substance serving as a biomarker, and observation of cells or the like.

REFERENCE SIGNS LIST

10: Plate
11, 12: Substrate
13: Detection space
14a, 14b: Port
15: Adhesive layer
16, 17, 18: Adapter Obviously, numerous modifications and variations of the present invention are possible in light of the above teachings. It is therefore to be understood that within the scope of the appended claims, the invention may be practiced otherwise than as specifically described herein.

What is claimed is:

1. An analytical device, comprising:
a plate comprising a first substrate, a second substrate facing the first substrate, and a side wall extending between the first and second substrates such that at least one detection space is formed between the second substrate and the first substrate and that the first substrate has a plurality of ports communicated with the detection space; and
an adapter having a first end and a second end on an opposite end with respect to the first end such that at least one of the first and second ends is configured to be fitted into at least one of the plurality of ports in the first substrate and has an abutment portion configured to abut against a surface of the second substrate inside the detection space and a cutout portion configured to form a flow path to the detection space inside the detection space when fitted into the one of the plurality of ports,
wherein at least one of the first and second substrates comprises a transparent material such that the detection space is observable from outside the plate, the plurality of ports includes a first port configured to deliver a liquid-containing substance into the detection space, and a second port configured to discharge the liquid-containing substance or a gas from the detection space.

2. The analytical device of claim 1, wherein the adapter comprises a tube having the first end configured to be fitted into the one of the plurality of ports, and the second end configured to be an open end with a larger diameter than the first end.

3. The analytical device of claim 1, wherein the plate is formed such that the at least one detection space comprises a plurality of detection spaces, the adapter has the first end configured to be fitted into the one of the plurality of ports communicated with the one of the detection spaces, and the second end configured to be fitted into the one of the plurality of ports communicated with another one of the detection spaces.

4. The analytical device of claim 1, wherein the adapter has an inner wall to which a reagent is fixed, and is configured to deliver the reagent into the detection space through the cutout portion.

5. The analytical device of claim 2, wherein the adapter has an inner wall to which a reagent is fixed, and is configured to deliver the reagent into the detection space through the cutout portion.

6. The analytical device of claim 3, wherein the adapter has an inner wall to which a reagent is fixed, and is configured to deliver the reagent into the detection space through the cutout portion.

7. The analytical device of claim 1, wherein the adapter has the first end configured to be fitted to the one of the plurality of ports, and the second end configured to be an open end or a closed end with a larger diameter than the first end.

8. The analytical device of claim 7, wherein the adapter includes an absorbing material and is configured to absorb an effluent discharged from the detection space through the cutout portion.

9. The analytical device of claim 1, wherein at least one of the first substrate and the second substrate has transparency that allows detection of fluorescence or luminescence in the detection space from outside the plate.

10. The analytical device of claim 1, wherein both the first substrate and the second substrate have transparency that allows detection of fluorescence or luminescence in the detection space from outside the plate.

11. The analytical device of claim 1, wherein the plate is formed such that the at least one detection space comprises a plurality of detection spaces, and the adapter has the first end configured to be fitted into the one of the plurality of ports communicated with the one of the detection spaces, and the second end configured to be fitted into the one of the plurality of ports communicated with another one of the detection spaces such that the adapter is configured to establish communication between the plurality of the detection spaces.

12. The analytical device of claim 1, wherein at least one of the first substrate and the second substrate has a surface having at least one pore positioned in the detection space, and the at least one pore has a capacity of 1 pl or less.

13. The analytical device of claim 1, further comprising:
a film or lid configured to cover one of the plurality of ports such that the film or lid is detachable or cut through.

14. The analytical device of claim 1, wherein the plate is configured to be heated such that the detection space is heated.

15. The analytical device of claim 1, wherein the side wall comprises an adhesive layer.

16. The analytical device of claim 1, wherein the plate is formed such that the at least one detection space comprises a plurality of detection spaces formed between the first and second substrates.

17. The analytical device of claim 1, wherein the at least one of the first and second ends is configured to fit into the at least one of the plurality of ports in the first substrate such that liquid does not leak when fitted into the at least one of the plurality of ports in the first substrate.

18. The analytical device of claim 1, wherein the adapter comprises an elastic material, and the at least one of the first and second ends is configured to fit into the at least one of the plurality of ports in the first substrate such that liquid does not leak when fitted into the at least one of the plurality of ports in the first substrate.

19. The analytical device of claim 1, wherein the plate has flat surfaces on exterior sides of the plate.

20. The analytical device of claim 1, wherein the at least one of the first and second ends has the cutout portion having a cross-sectional area equal to a cross-sectional area of a flow path of the detection space when fitted into the at least one of the plurality of ports in the first substrate.

* * * * *